United States Patent
Schaffner et al.

(10) Patent No.: US 10,405,979 B2
(45) Date of Patent: Sep. 10, 2019

(54) MEDICAL APPARATUS AND METHOD FOR HEART VALVE REPAIR

(71) Applicants: CoreMedic AG, Biel (CH); Universität Bern, Bern (CH)

(72) Inventors: Silvio Schaffner, Berlingen (CH); Louis Weidmann, Recherswill (CH); Rolf Vogel, Solothurn (CH); Stefan Guggisberg, Bern (CH); Andreas Mächler, Bern (CH); Stijn Vandenberghe, Bern (CH); Oliver Wüthrich, Hinterkappelen (CH); Thierry Carrel, Bern (CH); Alberto Weber, Gümligen (CH)

(73) Assignees: COREMEDIC AG, Biel (CH); UNIVERSITAT BERN, Bern (CH)

( * ) Notice: Subject to any disclaimer, the term of this patent is extended or adjusted under 35 U.S.C. 154(b) by 69 days.

(21) Appl. No.: 15/326,206

(22) PCT Filed: Jul. 9, 2015

(86) PCT No.: PCT/CH2015/000102
§ 371 (c)(1),
(2) Date: Jan. 13, 2017

(87) PCT Pub. No.: WO2016/008058
PCT Pub. Date: Jan. 21, 2016

(65) Prior Publication Data
US 2017/0202669 A1    Jul. 20, 2017

(30) Foreign Application Priority Data
Jul. 17, 2014    (CH) ........................................ 1086/14

(51) Int. Cl.
*A61F 2/24*    (2006.01)
*A61B 17/00*    (2006.01)
(Continued)

(52) U.S. Cl.
CPC ...... *A61F 2/2457* (2013.01); *A61B 17/00234* (2013.01); *A61B 17/0401* (2013.01);
(Continued)

(58) Field of Classification Search
CPC .... A61F 2/2457; A61F 2/2466; A61F 2/2427; A61F 2/2418; A61B 17/00234;
(Continued)

(56) References Cited

U.S. PATENT DOCUMENTS 8,828,053 B2 *    9/2014    Sengun .............. A61B 17/0401
606/232
2004/0003819 A1    1/2004    St. Goar et al.
(Continued)

FOREIGN PATENT DOCUMENTS

EP    2 277 457    1/2011
WO    2012/040865    4/2012

OTHER PUBLICATIONS

International Preliminary Report on Patentability dated Jan. 17, 2017, Application No. PCT/CH2015/000102.

*Primary Examiner* — Katherine M Shi
*Assistant Examiner* — Andrew P. Restaino
(74) *Attorney, Agent, or Firm* — Rankin, Hill & Clark LLP

(57) ABSTRACT

A surgical instrument for treating atrioventricular valve prolapse of the drained human heart, includes a handle for being held by a surgeon, a shaft extending distally from the handle, the shaft having a lumen open to a shaft distal end, a cannulated needle arranged in the shaft; with a distal end of the needle protruding from the shaft distal end at least in one possible needle position. The needle accommodates a first, distal implant equipped for being anchored in a papillary muscle, and a second, proximal implant shaped to hold on to a leaflet of an atrioventricular valve, the first and
(Continued)

second implants each including a chord connector portion for connecting the respective implant to an artificial chord. The apparatus further includes a trigger arrangement for releasing the first, distal implant upon a first release actuation and for releasing the second, proximal implant upon a second release actuation.

16 Claims, 3 Drawing Sheets

(51) Int. Cl.
    *A61B 17/04*     (2006.01)
    *A61B 17/062*     (2006.01)
    *A61B 17/064*     (2006.01)

(52) U.S. Cl.
    CPC ...... *A61B 17/0469* (2013.01); *A61B 17/0482* (2013.01); *A61B 17/0625* (2013.01); *A61F 2/2418* (2013.01); *A61F 2/2427* (2013.01); *A61F 2/2466* (2013.01); *A61B 17/0485* (2013.01); *A61B 17/0644* (2013.01); *A61B 2017/00243* (2013.01); *A61B 2017/00367* (2013.01); *A61B 2017/0417* (2013.01); *A61B 2017/0441* (2013.01); *A61B 2017/0464* (2013.01); *A61B 2017/0496* (2013.01)

(58) Field of Classification Search
    CPC ............ A61B 17/0625; A61B 17/0482; A61B 17/0469; A61B 17/0401
    USPC ........................................................ 623/2.11
    See application file for complete search history.

(56) References Cited

U.S. PATENT DOCUMENTS

| | | | |
|---|---|---|---|
| 2004/0249395 A1* | 12/2004 | Mikkaichi | A61B 17/0401 606/144 |
| 2007/0080188 A1 | 4/2007 | Spence et al. | |
| 2007/0118151 A1 | 5/2007 | Davidson | |
| 2008/0195126 A1 | 8/2008 | Solem | |
| 2010/0042147 A1 | 2/2010 | Janovsky et al. | |
| 2010/0234687 A1* | 9/2010 | Azarbarzin | A61B 17/29 600/201 |
| 2011/0022083 A1* | 1/2011 | DiMatteo | A61B 17/0401 606/232 |
| 2011/0172682 A1* | 7/2011 | Brady | A61B 17/0401 606/144 |
| 2012/0101522 A1* | 4/2012 | Megaro | A61B 17/06109 606/228 |
| 2013/0211427 A1* | 8/2013 | Castell Gomez | A61B 17/0401 606/144 |
| 2014/0031926 A1* | 1/2014 | Kudlik | A61B 17/0401 623/2.11 |
| 2014/0114404 A1* | 4/2014 | Gammie | A61B 17/0401 623/2.11 |

\* cited by examiner

MEDICAL APPARATUS AND METHOD FOR HEART VALVE REPAIR

BACKGROUND OF THE INVENTION

Field of the Invention

The invention generally relates to surgical devices for heart valve repair and, more particularly, relates to an instrument for repairing an atrioventricular heart valve, in particular the mitral heart valve, in open heart surgery (surgery of the drained heart, accessed through the split sternum, via an incision or sternotomy, minithoracotomy or from another direction). The invention further relates to an instrument set and to a surgical method.

Description of Related Art

Prolapses of a leaflet of the mitral valve into the left atrium and resulting valve insufficiency can cause serious dysfunctions of the heart. One reason for such prolapse is a damaging of the tendons (chordae tendinae) that connect the leaflets of the mitral valve to the papillary muscle through the left ventricle. Such a damage may, for example, be a result of a myocardial infarction or as a consequence of degenerative valve disease.

A repair of such a prolapse demands the leaflet or leaflets to be re-connected to the papillary muscle, for example by synthetic chords, such as Gore-tex® fibres.

There have been proposals to use minimally invasive techniques for the treatment of atrioventricular valve prolapses. US 2004/0003819 teaches to treat the prolapse by grasping two leaflets by a catheter and clamping them together. Also US 201070042147 teaches techniques of introducing a surgical suture by means of a catheter to treat this kind of prolapse. US 2008/195126 teaches methods for repairing the heart that are based on an anchor to be attached to the papillary muscle and a suture that is attached to the anchor and, for example, the leaflet or other place in the heart. WO 2012/040865 teaches approaches for temporary leaflet stabilization in minimally invasive surgery.

However, for the minimally invasive techniques, the temporary stabilization of the tissue portions in which implants are placed is still a challenge. Thus, open heart surgery is still preferred for carrying out atrioventricular valve repair operations. However, in open heart surgery, the handling and implantation of the very small implants used for these operations is still a challenge. Also, according to the state of the art, the leaflet is sutured to the implanted artificial chord, this demands high skills from the surgeon and is time consuming. Suturing of both sides (papillary muscle and leaflet) is challenging and not well defined and thus a challenge to surgeons.

SUMMARY OF THE INVENTION

It is therefore an object of the present invention to provide an instrument for treating atrioventricular valve regurgitation of the drained human heart, which instrument overcomes disadvantages of prior art approaches and brings about advantages in terms of handling (speed and accuracy) and security for the surgeon. It is a further object to provide an improved surgical method.

In accordance with an aspect of the invention, a surgical instrument for treating atrioventricular valve prolapse of the drained human heart is provided, the instrument comprising
- a handle for being held by a surgeon during a surgical operation;
- a shaft extending distally from the handle, the shaft comprising a lumen open to a shaft distal end;
- a cannulated needle arranged in the shaft; with a distal end of the needle protruding from the shaft distal end (at least in one possible needle position);
- the needle being equipped for accommodating, a first, distal implant equipped for being anchored in a papillary muscle, and a second, proximal implant shaped to hold on to a leaflet of an atrioventricular valve, the first and second implants each comprising a chord connector portion for connecting the respective implant to an artificial chord;
- the apparatus further comprising a trigger arrangement;
- wherein the trigger arrangement is equipped for releasing the first, distal implant upon a first release actuation; and
- wherein the trigger arrangement is equipped for releasing the second, proximal implant upon a second release actuation.

In this, the first and second release actuations may each be distinct actuations and thereby distinct from a single one-movement actuation during which firstly the distal implant and secondly the proximal implant is released. Rather, the first release actuation may be done by operating a lever or button or toggle switch or the like of the trigger arrangement, with this operation not causing the second release actuation, independent of the force applied.

In embodiments, the instrument may be a purely mechanical instrument, wherein the actuations are carried out manually (not excluding assistance by spring means), by purely mechanical means, without any electrically powered drive.

In a first group of examples, the first release actuation includes operating a trigger of the trigger arrangement until a first stop is reached. Then, in order for being able to cause the second release actuation, the operator has to perform an unlocking operation (the second release actuation unlocking operation), for example an unlocking operation that can only be done after the first release actuation. Then, the trigger is again operated for the second release actuation.

In embodiments, the prior to the first release actuation, also an unlocking operation (the first release actuation unlocking operation) has to be carried out.

For controlling the movements caused by the actuation, the trigger arrangement may especially include a sleeve with a slotted gate (slot with slot portions at an angle to each other) and a pin reaching through the slotted gate and being guided thereby. Therein, either the pin or the slotted gate has an axial position that is fixed relative to the handle and the other one is coupled to a part (for example the needle, if the actuation comprises retreatment of the needle) to be axially moved relative to the handle for actuation. The diameter of the pin and the width of the slots may be adapted to each other for allowing an easy relative movement while maintaining a good guidance.

Examples of this first group of examples include the requirement that for the unlocking operation, an element, for example a locking element, is rotated around the shaft axis relative to the handle and/or relative to the shaft until a first locking stop is reached in order to unlock the instrument for the first release actuation. After the first release actuation, the locking element may again have to be rotated relative to the handle and/or the shaft until a second locking stop is reached, and only then may the second release actuation be carried out.

In a second group of examples, alternatively, the trigger arrangement may include different operating elements for the first and second release actuations, such as two different levers, two different buttons, a lever and a button; or a toggle switch may need to be tipped to different sides etc.

In a group of embodiments, the release actuations may include retreating the needle relative to the handle and relative to the implants. To this end, the instrument may include a pusher arrangement extending through the needle and coupled to the handle so that the pusher arrangement's axial position is fix, the pusher arrangement cooperating with the implant parts so that the pusher arrangement keeps the axial position of the implants constant while the needle is retreated.

This group of embodiments features a substantial advantage: The surgeon may use the needle to pierce the tissue for implantation. No substantial piercing force has to act on the—often delicate—implants. Also, in the act of piercing the tissue with the needle, the implant to be released is placed in the appropriate depth in the tissue. The surgeon thus may adapt the implantation depth to the specific properties of the tissue by just choosing the appropriate piercing depth when he pierces by the needle.

The needle may include a mark allowing the surgeon to easily introduce the needle until it has reached the appropriate piercing depth.

Prior to being released, the proximal implant and the distal implant may be arranged directly in the cannulation of the needle. An inner diameter of the cannulation is then, for example, about 1 mm, and preferably does not exceed 1.2 mm.

Alternatively, in embodiments, the instrument includes, between the implants (and, if applicable the pusher arrangement) and the needle a further layer, namely a tube. This tube or protection tube may have a non-cutting distal edge. In these embodiments, the trigger arrangement may be equipped for carrying out a further actuation prior to the first release actuation, namely a first actuation being a needle retreatment actuation. In this needle retreatment actuation, the needle is retreated until the distal end of the needle is proximally of the distal edge of the tube. After the needle retreatment actuation, the first and second release actuations may be carried out, which actuations may include retreating the tube, possibly at least to some extent together with the needle, to consecutively release the distal and proximal implant parts whose axial positions relative to the handle are kept constant by the pusher. The needle and the tube may be retreated together in both release actuations or in the first release actuation or in the second release actuation, or it would also be possible to retreat only the tube by the release actuations since after the second release actuation the instrument is removed anyway and the protection by the sleeve is not necessary any more.

The tube after the first actuation (needle retreatment actuation) protects tissue and other objects, especially the chord, from being damaged by the sharp cutting edges of the needle during subsequent surgical steps, especially the step of releasing the proximal implant.

The tube can have a flush end (not beveled like the needle), that is, an end surface that is orthogonal to the longitudinal axis of the tube. This aids in accomplishing that the deployable features of the distal anchor are deployed simultaneously. This allows for symmetric ejection of the anchor from of the device.

The tube can ensure that after full deployment the needle is less exposed, preventing injury of the handler and other persons.

The tube can prevent scratching between the inside of the needle and the components of the implant.

In these alternative embodiments with the tube between the needle and the implant, an inner diameter of the needle may be somewhat larger. The inner diameter of the tube may then be about 1 mm and not exceed 1.2 mm Alternatively to a protection tube being arranged between the implants (and the pusher) on the one hand and the needle on the other hand, a protection tube may also be arranged around the needle, in which case the implants again are arranged directly in the cannulation of the needle. The function and the movements relative to the needle (in the first actuation) and the implants (in the first and second release actuations) remain the same.

The proximal implant and the distal implant may especially be arrangeable axially beside each other, with the distal implant part distally of the proximal implant part. This does not exclude an arrangement that keeps the implant parts at a certain distance from each other, for example by some kind of an intermediate piece. Neither does it exclude an arrangement where there is some overlap between the proximal implant and the distal implant.

The proximal implant and the distal implant may be pre-connected by the chord, for example by being clamped, knotted, welded or glued. The cord herein is often referred to as "artificial chord", however, it may also be an allograft or autograft or xenograft chord. The length of the connection between the implant parts may be adjusted to the distance between the leaflet and the papillary muscle in a closed state of the atrioventricular valve.

The shaft of the instrument may be fixed relative to the handle. For example, it has a straight portion extending from the handle, and a distal end portion being bent in a way that allows a better maneuverability for carrying out the intended surgical procedure. This angle (5°-25°, especially 10°-20°, in particular around 15°, i.e.) 12°-18°) is chosen based on the access that a surgeon can obtain during thoracoscopic surgery and also related to the angle between the mitral valve and the papillary muscles.

Because in embodiments the needle is axially movable within the shaft, such axial movements include moving an element connected to the needle (or the needle itself) around a bend. To this end, the needle may be proximally connected to wire or tubing elements that are bendable but have a fixed axial length. Such wire or tubing elements, for example slotted tubes, are well-known from minimally invasive surgery. Also other elements (pusher, tube if applicable) protruding distally from the shaft may proximally be connected to such wires or tubes with a fixed axial length.

The length of the shaft may be determined so it can be used both via sternotomy and in thoracoscopic procedures. In other words, the length of the shaft may be such as to allow access to the left ventricle of the heart of an average-sized grown-up human from the right lateral side through the thorax from outside of the thorax. The length of the shaft in particular may be between 20 cm and 30 cm.

The invention also concerns a method for treating atrioventricular valve prolapse of the drained human heart, the method including the steps of
  piercing a leaflet of the drained heart by a cannulated needle, thereby generating a piercing hole in the leaflet;
  advancing the needle through the piercing hole to muscle tissue of the heart;
  penetrating the muscle tissue of the heart with the needle to a pre-determined depth;
  releasing a distal implant from within the needle into the muscle tissue;
  retreating the needle until a distal end thereof is positioned relative to the piercing hole, for example proximally thereof, or with the end approximately flush therewith or with the needle protruding distally not more than a proximal implant characteristic dimension;

releasing a proximal implant from within the needle to adhere to the leaflet, and causing the proximal implant and the distal implant to be connected to each other by a chord;

removing the needle.

Thus, in accordance with this method, for surgery of the opened, drained, beating or non-beating heart a distal implant to be anchored in the muscle tissue for connecting the leaflet thereto is introduced via a piercing hole in the leaflet.

BRIEF DESCRIPTION OF THE DRAWINGS

Hereinafter, principles and embodiments of the invention are described referring to drawings. In the drawings, same reference numbers refer to same or analogous elements.

The drawings show.

DETAILED DESCRIPTION OF THE INVENTION

Figure 1:
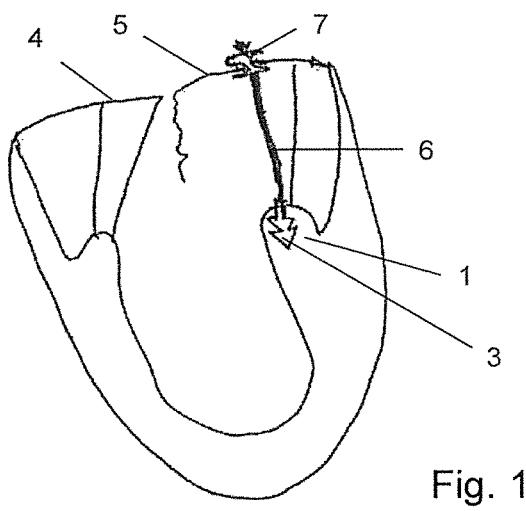
FIG. 1 in part, a section through the left ventricle of a human heart with a distal and a proximal implant connected by a chord stabilizing the mitral valve.

FIG. 1 shows, in part, a section through the left ventricle of the human heart with the mitral valve 4, 5. One leaflet 5 of the mitral valve has, without the surgical treatment discussed herein, the potential of prolapsing into the left atrium (not shown) because a chord 6 for connecting the leaflet 5 to the papillary muscle 1 is damaged.

Figure 2:
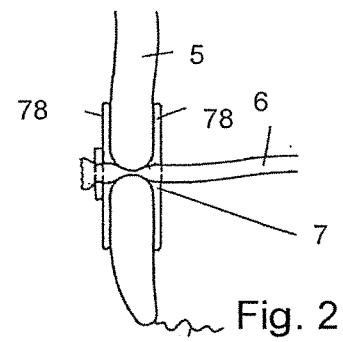
FIG. 2 the attachment of the proximal implant to the leaflet.

Instead of the damaged chord, in the illustrated configuration the heart is provided with an artificial chord extending between a distal implant 3 anchored in the papillary muscle and a proximal implant 7 attached to the leaflet. The distal implant may, for example, have a tip and a plurality of barbs anchoring it safely in the muscle tissue. FIG. 2 depicts the attachment of the proximal implant 7 to the leaflet in more detail. The leaflet is pierced, and the proximal implant 7 has a waist portion with two disc portions 78. The proximal implant 7 may be configured like a proximal implant of the kind described in WO 2012/040865 for being affixed to a leaflet of an atrioventricular valve of the human heart The artificial chord connects the proximal implant with the distal implant. It may be tied to the implants by being knotted to them or attached in a knotless manner, for example by being clamped by at least one of them, or tied by another technique. The length of the chord may be adjustable.

Figure 3:
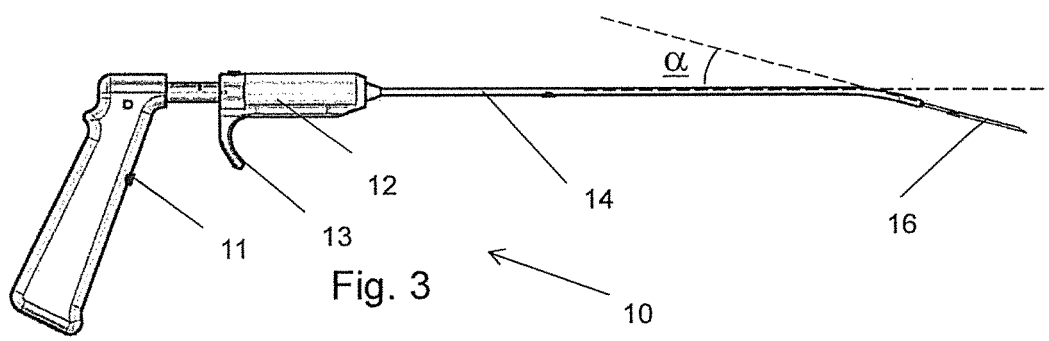
FIG. 3 a side view of an embodiment of the instrument.
Figure 4:
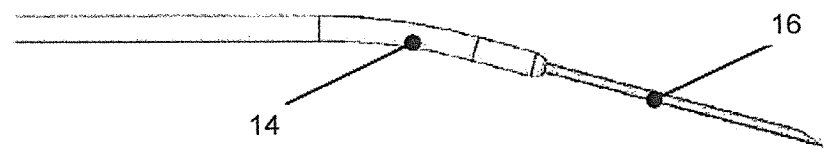
FIG. 4 a distal portion of the shaft with the needle protruding therefrom.

FIG. 3 depicts a side view of an embodiment of the instrument. The instrument includes a handle 11 for the surgeon, and the handle is dimensioned so that the surgeon can take and firmly hold the whole instrument in one hand. Distally from the handle, a shaft 14 extends. A trigger 12 with a trigger lever 13 is coupled to the shaft portion, in a manner described hereinafter in more detail. As also seen in FIG. 4, from the distal end of the shaft 14 protrudes the distal end of a needle 16. The shaft is bent towards its distal end by an angle of α of about 15°.

Figure 5:
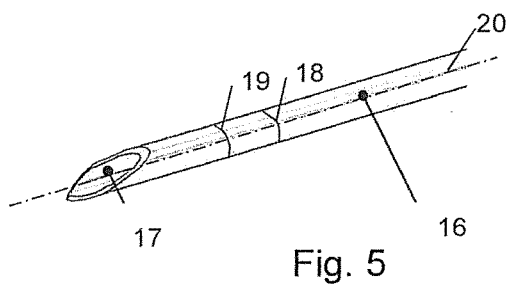
FIG. 5 the distal end of the needle.

A special optional feature of the needle is shown in FIG. 5. The needle contains on its outer surface at least one mark, namely two marks 18, 19. The marks may, for example, be marks laser etched or engraved on the needle. As known from surgical needles, the needle 16 ends in a bevel tip 17. The needle is cannulated and defines an axis 20. In this text, generally, an axial position is a position along the axis defined by the cannulation of the needle, the axis following any bends of the needle etc.

In contrast to the depicted version, the two marks may be different so that the surgeon can immediately see which mark she/he is looking at. For example, one mark may be represented by a double line, whereas the other mark is a single line.

Figure 6:
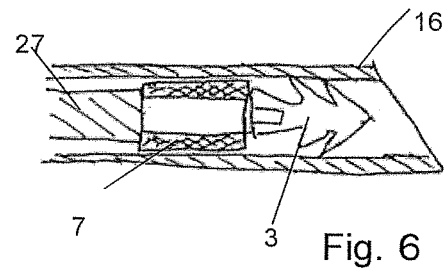
FIG. 6 schematically and in section, a distal end of the needle with the loaded implants.

FIG. 6 shows, schematically and in section, a distal end of the needle 16. Inside the needle, the distal implant 3 and the proximal implant 7 (that may be self-expanding as explained in WO 2012/040865) are arranged axially beside each other. Optionally also the artificial chord may be present between in the lumen of the needle, and it may, for example, be pre-assembled with the distal implant and, for example, be guided through the proximal implant. The needle also contains a pusher 27—here arranged proximally of the proximal implant. The pusher is depicted as a wire-like element; in other versions, the pusher may also be cannulated.

In the embodiment described here, the pusher 27 has a fixed axial position relative the handle. For example, the pusher may be a wire or tube the proximal end of which is fixed relative to the handle. The needle is retractable, thus axially movable relative to the handle. However, concepts described in this text also apply to systems with a fixed needle and an axially movable pusher.

Figure 7:
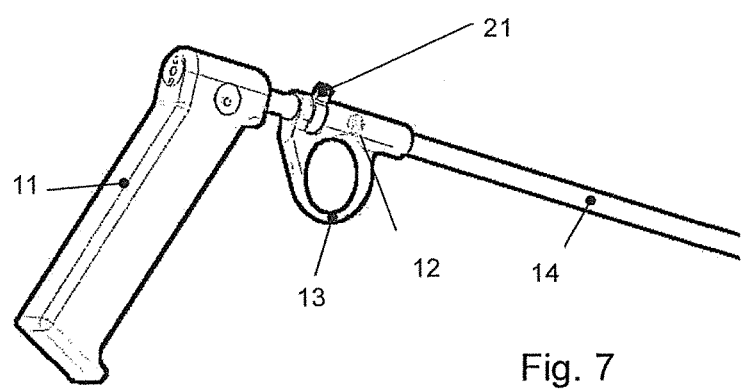
FIG. 7 a proximal part of a different embodiment of the instrument.
Figure 8:
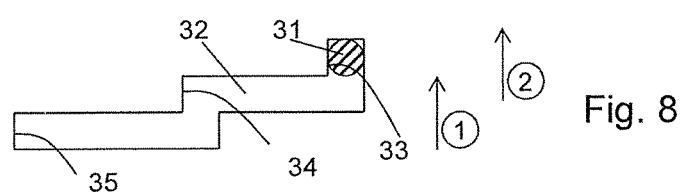
FIGS. 8 and 9 possible locking mechanisms with slotted gates in rotatable sleeves.

As shown in FIG. 7, illustrating a slightly different embodiment compared to FIG. 3, the trigger 12 in addition to the trigger lever 13 also includes a locking switch 21. A possible locking mechanism is schematically depicted in FIG. 8. In FIG. 8, axial directions are horizontal, and up-down corresponds to circumferential directions.

This mechanism includes a structure, such as a pin 31, of the first, fix element (here: coupled to the pusher or the shaft) or of the movable element (here: coupled to the needle)—sliding relative to a slot 32 of the other one of the fix element and the movable element (second element).

As shown in FIG. 8, the slot is formed to have a plurality of different stop faces.

In an initial, locked position, the pin is incapable of axially moving relative to the second element. Especially, retreatment of the needle is prevented by a first stop face 33. By actuating the locking switch 12 by a pivoting movement, the second element is rotated relative to the first element (arrow (1)), and the surgeon may axially move the first and second elements relative to one another until a second stop face 34 is reached by the pin. A further needle retreatment movement is not possible until the locking switch is actuated a second time, whereby the second element is rotated relative to the first element a second time (arrow (2)). Then, again a relative axial movement (retreatment movement of the needle) may be caused until the pin reaches a third stop face 35.

Figure 9:
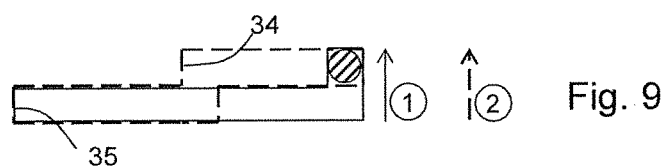

Similarly, instead of two unlocking rotational movements of one second element, it would also be possible to use two layers of slotted elements, as schematically illustrated in FIG. 9. For a first unlocking operation, a first one of the slotted elements (shown in solid lines in FIG. 9) is rotated (arrow (1)), wherein the second one of the slotted elements (dashed lines)) is held still. This releases the pin 31 for an axial movement relative to the slotted elements until the pin abuts against a first stop face 34 being a stop face of the second slotted element. Then, for the second unlocking operation, the second slotted element is rotated (arrow (2)), and the pin can slide relative to the slotted elements until the pin reaches a second stop face 35 formed by the first and/or the second slotted element. In this, for example, one of the slotted elements may be the needle and the other one of the slotted elements may be a guiding sleeve axially moving together with the needle.

The principle of FIG. 9 may, for example, be implemented by the first and second slotted elements being rotatable sleeves. Rotation of the locking switch causes an overlap in the slots of the rotating sleeves that determines how far each part can be retracted.

While in many embodiments implementing the principles of FIG. 8 or 9, actuation will include moving the pin and holding the axial positions of the slotted element(s), such as rotatable sleeves, still, it could also be the other way round.

Figure 10:
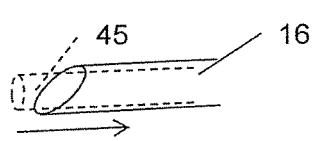
FIG. 10 the principle of a protection tube.

FIG. 10 shows the principle of the protection tube 45 that protects, after the piercing, from the needle. In embodiments with this protection tube 45, the needle 16 is retracted (arrow) until the distal-most spot of the instrument is formed by the protection tube 45. Thereafter, the release actuations are carried out by retracting the needle and the protection tube together, as described in the previous embodiments.

Figure 11:
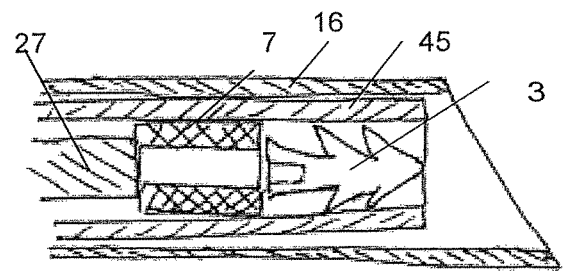
FIG. 11 schematically and in section, the distal end of a loaded instrument that includes such a protection tube.

FIG. 11 illustrates, schematically and in section, the distal end of an instrument that includes such a protection tube. The distal implant 3 and the proximal implant 7 are arranged inside the tube, again with a pusher 27 for ensuring a relative axial movement of the tube 42 and the implants 3, 7. Also in these embodiments, the pusher may have a fixed axial position relative to the handle.

Figure 12:
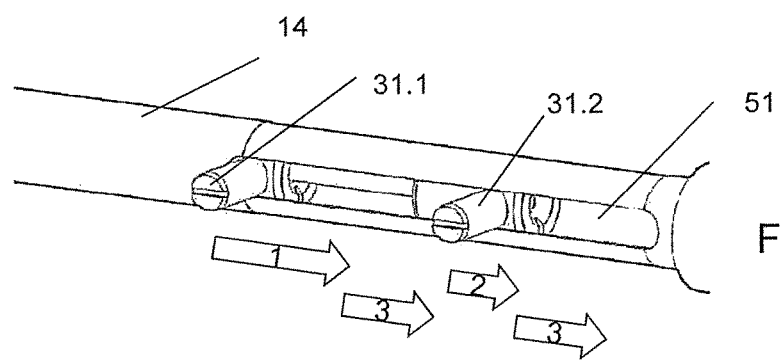
FIGS. 12-14 a locking mechanism for an embodiment including a protection tube.
Figure 13:
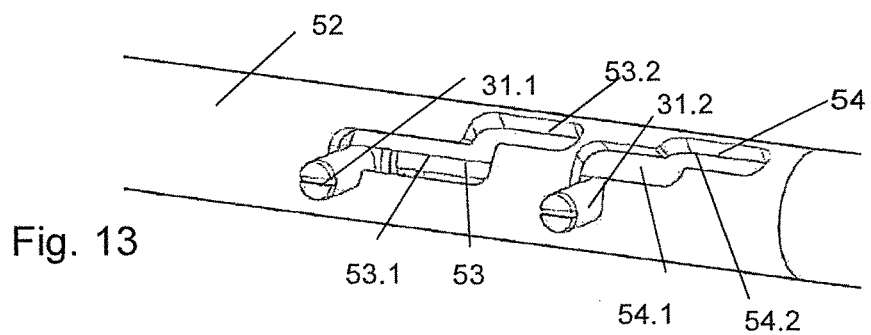
Figure 14:
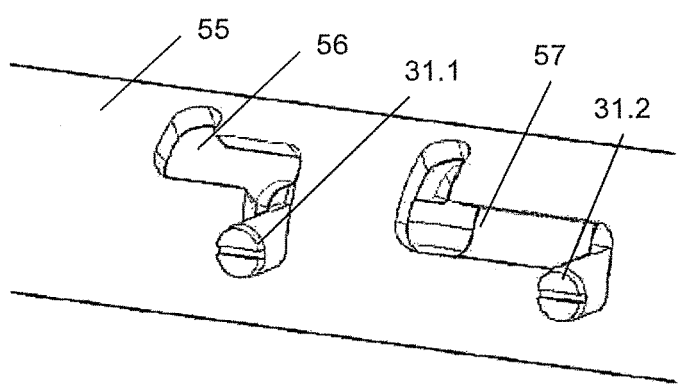

FIGS. 12-14 show a locking mechanism for this embodiment. Also in this embodiment, locking is actuated by rotations of the locking switch.

When the locking switch is rotated to a first position, the lever and the connected needle are set free to enable the first pull of the lever 13. A second actuation of the locking switch enables the second pull, which acts on the tube, and a third rotation enables the third pull of the lever acts on both, the needle and the tube.

FIG. 12 shows the shaft (that has a fix position relative to the lever and the pusher (not shown in FIG. 12) with a first pin 31.1 coupled to the needle and a second pin 31.2 coupled to the tube. The shaft has a slot 51 enabling a relative axial movement of the pins while fixing the relative orientation.

FIG. 13 shows the shaft covered by an inner rotation sleeve 52 with slots 53, 54. FIG. 14 in addition shows an outer rotation sleeve 55.

The outer rotation sleeve is rotationally coupled to the inner rotation sleeve, for example by a key (such as a pin-like element of one rotation sleeve protruding into a groove of the other rotation sleeve) but axially movable. The rotation sleeves thus rotate together. The inner rotation sleeve has a fixed axial position. The outer rotation sleeve may be coupled to the lever and is used to pull along the pins 31.1, 31.2 for their axial movements.

All Figures show the instrument in the initial position, i.e. before the actuations.

The three actuation steps in this embodiment are as follows:

By the first actuation (first pull of the lever 13), after a first unlocking operation that includes rotating the sleeves, the outer sleeve is retreated, taking along the first pin 31.1 that slides in the long groove portion 53.1 of the inner sleeve. The second pin 31.2 coupled to the tube is not taken along, due to the groove 57 in the outer sleeve and also because it is blocked in this orientation by the inner sleeve (double security preventing the tube from being retracted with the needle).

The second unlocking operation includes again rotating the sleeves until the second pin stops the rotation and is free to be retracted along the short groove portion 54.1. The second actuation—being the first release actuation—includes again retreating the outer sleeve, taking along the second pin 31.2, thereby retreating the tube and releasing the distal implant. The first pin 31.1 is not taken along but allowed to stand still because of the groove 56 in the outer sleeve and also because it is blocked in this orientation by the inner sleeve.

The third unlocking operation again includes rotating the sleeves. In the third actuation, again the outer sleeve is retracted, thereby taking along both, the first and the second pin, which pins can slide in the respective second groove portions 53.2, 54.2.

The arrows in FIG. 12 schematically show the retreatment of the pins in the first, second and third actuation.

Alternatively, it would also be possible to cause retreatment of both pins in the second and third actuations, or to cause retreatment of both pins in second actuation and only of the second pin in the third actuation. If the needle in the first actuation is retreated to a sufficient extent (long path), the second and third actuations may also both include retreatment just of the second pin, coupled to the tube.

A surgical operation is carried out as follows:

The instrument is loaded, wherein the distal implant is placed proximally of the distal end of the needle or the tube, respectively, and the proximal implant is axially besides the distal implant proximally thereof. In embodiments in which the distal implant and the proximal implant are pre-assembled with the chord, the chord may, for example, extend in a loop proximally of the proximal implant and with one end connected to the distal implant.

The operation site is prepared, either by sternotomy or for a thoracoscopic procedure. The length of the shaft 14 is adapted to the anatomy so that the heart valve of the drained heart can also be accessed, from the right-hand side, through the not opened thorax.

Thereafter, firstly the leaflet is punctured by the needle, and then the needle is guided through the puncture of the leaflet into the papillary muscle that is also punctured. The mark 18, or, if two marks are present, the more proximal mark 18 is used to determine how deep the needle pierces the tissue: if the mark 18 is flush with the tissue surface, the correct position is assumed.

Then, in the embodiments that include a protection tube, the needle is retracted by the first actuation. The second, more distal mark 19 may serve to control that the depth is still appropriate after the retraction of the needle. If necessary, the piercing depth can be re-adjusted using the distal mark after the first actuation.

Subsequently in both, embodiments with the protection tube and embodiments without the protection tube, the first release actuation (being the second actuation in embodiments with the protection tube) is carried out. Thereby, the distal implant is released. The whole device is then retracted with the distal implant remaining anchored in the muscle tissue and, if applicable with the chord tied thereto.

After a desired position relative to the leaflet has been achieved (this relative position will depend on the nature of the proximal implant; it will approximately be a position in which the distal end of the protection tube, or the needle, respectively, is at the spot where the leaflet is pierced), the second release actuation is carried out. Thereafter, the instrument is retracted.

What is claimed is:

1. A surgical instrument for treating atrioventricular valve prolapse of the drained human heart, the instrument comprising:
    a first distal implant and a second, proximal implant;
    a handle for being held by a surgeon during a surgical operation;
    a shaft extending distally from the handle, the shaft comprising a lumen open to a distal end of the shaft;
    a cannulated needle arranged in the shaft, a distal end of the needle protruding from the distal end of the shaft at least in one possible needle position;
    the needle receiving or accommodating the first, distal implant equipped for being anchored in a papillary muscle, and the second, proximal implant shaped to hold on to a leaflet of an atrioventricular valve, the first and second implants each comprising a chord connector portion for connecting the respective implant to an artificial chord;
    The apparatus further comprising a trigger arrangement;
    wherein the trigger arrangement is equipped for releasing the first, distal implant upon a first release actuation;
    wherein the trigger arrangement is equipped for releasing the second, proximal implant upon a second release actuation; and
    further comprising a protection tube, the protection tube being axially movable relative to the needle and relative to the proximal and distal implants, the protection tube being arranged inside the cannulated needle and around the proximal and distal implants.

2. The instrument according to claim 1, wherein the trigger arrangement comprises a lever, wherein for the first release actuation the lever is operated until it reaches a first release actuation stop position, wherein the second release actuation comprises operating the lever until it reaches a second position, and wherein moving the lever to the second position is only possible upon an unlocking operation.

3. The instrument according to claim 2, wherein moving the lever to the first release actuation stop position is only possible upon a prior unlocking operation.

4. The instrument according to claim 2, wherein the trigger arrangement further comprises a locking element rotatable about an axis of the shaft relative to the handle.

5. The instrument according to claim 1, wherein the first release actuation and the second release actuation both comprise retreating the needle relative to the handle.

6. The instrument according to claim 5, comprising a pusher arrangement extending into the needle from the proximal side and coupled to the handle so that the pusher arrangement's axial position is fixed relative to the handle, the pusher arrangement cooperating with the implants so that the pusher arrangement keeps the axial position of the implants constant while the needle is retreated.

7. The instrument according to claim 1, wherein the trigger arrangement comprises a sleeve with a slotted gate and a pin, reaching through the slotted gate and being guided thereby, wherein one of the pin and the slotted gate has an axial position that is fixed relative to the handle and the other one is coupled to a part to be axially moved relative to the handle for actuation.

8. The instrument according to claim 1, wherein the trigger arrangement is equipped for retreating the needle relative to the protection tube and the proximal and distal implants upon a first actuation prior to the first release actuation.

9. The instrument according to claim 1, wherein the first release actuation comprises retreating the protection tube or the needle or both, and wherein the second release actuation comprises retreating the protection tube or the needle or both.

10. The instrument according to claim 9, wherein the first and second release actuations each comprise retreating at least the protection tube.

11. The instrument according to claim 1, wherein an inner diameter of the protection tube does not exceed 1.2 mm.

12. The instrument according to claim 1, wherein an outer diameter of the needle does not exceed 1.6 mm.

13. The instrument according to claim 1, wherein the shaft has a straight portion extending from the handle and a distal end portion, and wherein the distal end portion is at an angle of between 5° and 25° to the straight portion.

14. The instrument according to claim 1, wherein the shaft portion has a pre-defined length of 20-30 cm.

15. The instrument according to claim 1, wherein the first, distal implant, and the second, proximal implant are arranged axially beside each other within the cannulated needle, with the distal implant being arranged distally of the proximal implant.

16. The arrangement according to claim 15, wherein the distal implant and the proximal implant being arranged within the cannulated needle are connected to each other by an artificial or allograft or autograft or xenograft chord.

* * * * *